United States Patent

Scherhag et al.

(10) Patent No.: US 7,396,959 B2
(45) Date of Patent: Jul. 8, 2008

(54) PROCESS FOR PREPARING SYMMETRICAL AND UNSYMMETRICAL N,N-DIHYDROCARBYLHYDROXYLAMINES

(75) Inventors: Gunter Scherhag, Heidelberg (DE); Lars Wittenbecher, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 11/607,626

(22) Filed: Dec. 1, 2006

(65) Prior Publication Data

US 2007/0129574 A1 Jun. 7, 2007

(30) Foreign Application Priority Data

Dec. 2, 2005 (DE) .................. 10 2005 057 715

(51) Int. Cl.
C07C 239/12 (2006.01)
C07C 291/00 (2006.01)
(52) U.S. Cl. .................. 564/301; 564/300; 564/259
(58) Field of Classification Search .......... 564/300, 564/301, 259
See application file for complete search history.

(56) References Cited

U.S. PATENT DOCUMENTS 4,876,300 A   10/1989   Seltzer et al.
5,144,075 A * 9/1992   Suhadolnik .................. 564/301

FOREIGN PATENT DOCUMENTS

EP   0 495 756   7/1992

* cited by examiner

*Primary Examiner*—Yvonne Eyler
*Assistant Examiner*—Yate' K Cutliff

(74) *Attorney, Agent, or Firm*—Connolly Bove Lodge & Hutz LLP

(57) ABSTRACT

A process for preparing N,N-dihydrocarbylhydroxylamines of the general formula (I)

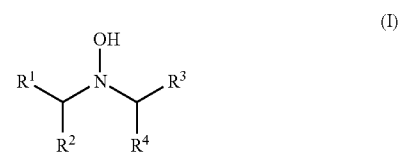

where $R^1$, $R^2$, $R^3$ and $R^4$ are selected independently from among hydrogen, aliphatic, cycloaliphatic, heteroaromatic and aromatic radicals, or $R^1$ and $R^2$ and/or $R^3$ and $R^4$ are joined to form a ring, and not more than one radical among $R^1$, $R^2$, $R^3$ and $R^4$ is hydrogen, which comprises the steps a) reaction of hydroxylamine $H_2NOH$ or a salt of hydroxylamine with a compound of the general formula (II) or (III)

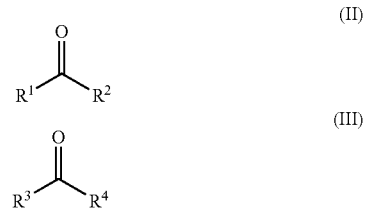

where $R^1$, $R^2$, $R^3$ and $R^4$ are as defined in formula (I), b) hydrogenation of the compound formed in step a) in the presence of a catalyst, c) further reaction of the compound formed in step b) with a compound of the general formula (II) or (III) and hydrogenation of the reaction mixture in the presence of a catalyst and d), if appropriate, reaction of the salt of the dihydrocarbylhydroxylamine formed in step c) with a base.

16 Claims, No Drawings

PROCESS FOR PREPARING SYMMETRICAL AND UNSYMMETRICAL N,N-DIHYDROCARBYLHYDROXYLAMINES

BACKGROUND OF THE INVENTION

Processes for preparing N,N-dihydrocarbylhydroxylamines are known from the prior art.

N,N-dihydrocarbylhydroxylamines are typically prepared by oxidation of the nitrogen atom of the corresponding amines. A disadvantage of the process mentioned is the use of the expensive N,N-dialkylamines as starting compounds.

U.S. Pat. No. 4,876,300 discloses the use of long-chain N,N-dialkylhydroxylamines as stabilizers for polyolefin compositions during their preparation. It is also disclosed that the long-chain N,N-dialkylhydroxylamines used can be prepared by various methods, for example:

- oxidation of the corresponding secondary amines by means of aqueous hydrogen peroxide solution in order to obtain the corresponding N,N-dialkyl-hydroxylamines directly,
- addition of the corresponding secondary amine onto α,β-unsaturated compounds, for example alkyl acrylates, to obtain the corresponding Michael addition product which is converted in a further process step by means of aqueous hydrogen peroxide solution into the corresponding tertiary amine oxide, and subsequent elimination of the α,β-unsaturated compound to give the N,N-dialkylhydroxylamine,
- metathesis reaction between an alkyl halide and a hydroxylamine in the presence of an alkaline compound such as sodium amide, or reaction of an amine with a peroxy compound such as benzoyl peroxide, followed by hydrolysis of the compound formed as an intermediate to give the corresponding hydroxylamine.

EP 0 495 756 A1 discloses a process for preparing N,N-dihydrocarbylhydroxylamines $(RCH_2)_2NOH$ from aldehydes and hydroxylamine hydrochloride under hydrogenation conditions in a single-stage process. For this purpose, two equivalents of aldehyde are reacted with hydroxylamine hydrochloride in the presence of hydrogen and a suitable noble metal catalyst to give the corresponding N,N-dihydrocarbylhydroxylamines.

BRIEF SUMMARY OF THE INVENTION

The present invention relates to a process for preparing N,N-dihydrocarbylhydroxylamines. It is an object of the present invention to provide a process for preparing symmetrical and unsymmetrical N,N-dihydrocarbylhydroxylamines $(R^1R^2CH)(R^3R^4CH)NOH$, where at least three of the radicals $R^1$, $R^2$, $R^3$ and $R^4$ are not hydrogen, which is simple to carry out, uses inexpensive starting materials and makes it possible to prepare N,N-dihydrocarbylhydroxylamines which are doubly substituted on at least one of the carbon atoms adjoining the hydroxylamine group.

This object is achieved by a process for preparing N,N-dihydrocarbylhydroxylamines of the general formula (I)

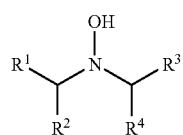

(I)

where $R^1$, $R^2$, $R^3$ and $R^4$ are selected independently from among hydrogen, branched or unbranched, aliphatic, cycloaliphatic, heteroaromatic and aromatic radicals having from 1 to 32 carbon atoms, or $R^1$ and $R^2$ and/or $R^3$ and $R^4$ are joined to form a ring having a total of from 3 to 12 carbon atoms, and not more than one radical among $R^1$, $R^2$, $R^3$ and $R^4$ is hydrogen, which comprises the following steps:

a) reaction of hydroxylamine $H_2NOH$ or a salt of hydroxylamine with a compound of the general formula (II) or (III)

(II)

(III)

where $R^1$, $R^2$, $R^3$ and $R^4$ are as defined in formula (I), b) hydrogenation of the compound formed in step a) in the presence of a catalyst comprising a noble metal to a hydrogen consumption of from 60 to 130 mol % of theory, giving the corresponding monohydrocarbylhydroxylamine or the salt of the corresponding monohydrocarbylhydroxylamine, c) further reaction of the compound formed in step b) with a compound of the general formula (II) or (III) and hydrogenation of the reaction mixture in the presence of a catalyst comprising a noble metal in an aqueous medium to a hydrogen consumption of from 60 to 130 mol % of theory, forming the corresponding dihydrocarbylhydroxylamine or the salt of the corresponding dihydrocarbylhydroxylamine, and d) if a salt of hydroxylamine was used in step a), reaction of the salt of dihydrocarbylhydroxylamine formed in step c) with a base.

In the process of the present invention, N,N-dihydrocarbylhydroxylamines of the general formula (I)

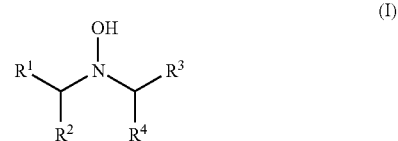

(I)

where $R^1$, $R^2$, $R^3$ and $R^4$ are selected independently from among hydrogen, branched or unbranched, aliphatic, cycloaliphatic, heteroaromatic and aromatic radicals having from 1 to 32 carbon atoms, or $R^1$ and $R^2$ and/or $R^3$ and $R^4$ are joined to form a ring having a total of from 3 to 12 carbon atoms, and not more than one radical among $R^1$, $R^2$, $R^3$ and $R^4$ is hydrogen are prepared.

In a preferred embodiment, none of the radicals $R^1$, $R^2$, $R^3$ and $R^4$ is hydrogen, i.e. the compounds of the general formulae (II) and (III) are ketones.

For the purposes of the present invention, an aliphatic radical is a branched or unbranched saturated or unsaturated radical having from 1 to 32 carbon atoms. In a preferred embodiment, $R^1$, $R^2$, $R^3$ and $R^4$ are each, independently of one another, a branched or unbranched, aliphatic radical having from 1 to 12, particularly preferably 1 to 6, carbon atoms, for example a radical selected from the group consisting of methyl, ethyl, propyl, isopropyl, butyl, isobutyl, tert-butyl, pentyl and hexyl. These aliphatic radicals may be substituted by functional groups selected from the group consisting of amine, aldehyde, ketone, ether, amine, imine, amide, imide and halide groups.

For the purposes of the present invention, a cycloaliphatic radical is a branched or unbranched saturated or unsaturated cyclic radical having from 3 to 32 carbon atoms. In a further preferred embodiment, $R^1$, $R^2$, $R^3$ and $R^4$ are each, independently of one another, a cycloaliphatic radical having from 3 to 8 carbon atoms, for example cyclopentyl or cyclohexyl, which may in turn be substituted by aliphatic radicals having from 1 to 6 carbon atoms or functional groups selected from the group consisting of amine, aldehyde, ketone, ether, amine, imine, amide, imide and halide groups.

For the purposes of the present invention, a heteroaromatic radical is a saturated or unsaturated cyclic radical which has from 3 to 32 carbon atoms and additionally has heteroatoms selected from the group consisting of N, O, P and S in the ring. In a further preferred embodiment, $R^1$, $R^2$, $R^3$ and $R^4$ are each, independently of one another, a heteroaromatic radical which has from 3 to 8 carbon atoms and heteroatoms selected from the group consisting of N, O, P and S and may in turn be substituted by aliphatic radicals having from 1 to 6 carbon atoms, functional groups and/or halogens, for example fluorine, chlorine, bromine.

For the purposes of the present invention, an aromatic radical is an aromatic, monocyclic or polycyclic radical having from 4 to 32 carbon atoms. In a further preferred embodiment, $R^1$, $R^2$, $R^3$ and $R^4$ are each, independently of one another, an aromatic radical which has from 5 to 8 carbon atoms and may in turn be substituted with one or more aliphatic radicals having from 1 to 6 carbon atoms or functional groups. Preferred aromatic radicals are, for example, benzyl, toluyl, xylyl.

In a further preferred embodiment, $R^1$ and $R^2$ and/or $R^3$ and $R^4$ in each case form a ring which has a total of from 3 to 12 carbon atoms and may in turn be substituted by linear or branched alkyl radicals having from 1 to 6 carbon atoms and functional groups, selected from the group consisting of amine, aldehyde, ketone, ether, amine, imine, amide, imide and halide groups. Preference is given to $R^1$ and $R^2$ and/or $R^3$ and $R^4$ in each case forming a ring having 5, 6, 7 or 8 carbon atoms.

In a preferred embodiment, the radicals $R^1$, $R^2$, $R^3$ and $R^4$ in the general formula (I) are identical.

In a further preferred embodiment, the radicals $R^1$ and $R^2$ and the radicals $R^3$ and $R^4$ are in each case identical and the radicals $R^1$ and $R^3$ and the radicals $R^2$ and $R^4$ are different from one another.

In a further preferred embodiment, $R^1/R^2$ and $R^3/R^4$ in the compounds of the general formulae (I), (II) and (III) in each case form a saturated ring having 6 carbon atoms.

In a further preferred embodiment, the radicals $R^3$ and $R^4$ form a saturated ring having 5, 6, 7 or 8 carbon atoms and the radicals $R^1$ and $R^2$ are identical, for example methyl or ethyl.

Furthermore, it is preferred that $R^1$, $R^2$, $R^3$ and $R^4$ in the general formulae (I), (II) and (III) are selected independently from the group consisting of methyl, ethyl, n-propyl, isopropyl, n-butyl, isobutyl and pentyl.

Very particular preference is given to preparing an N,N-dihydrocarbylhydroxylamine of the general formula (I) in which $R^1$ and $R^2$ and $R^3$ and $R^4$ in each case form a saturated ring having 6 carbon atoms or $R^1$ and $R^2$ are each methyl and $R^3$ and $R^4$ form a saturated ring having 6 carbon atoms or $R^1$, $R^2$, $R^3$ and $R^4$ are each methyl by the process of the invention, i.e. cyclohexanone and acetone are particularly preferably used as compounds of the general formulae (II) and (III).

Very particular preference is thus given to preparing dicyclohexylhydroxylamine (IV), cyclohexylisopropylhydroxylamine (V), diisopropylhydroxylamine (VI) or mixtures thereof by the process of the present invention.

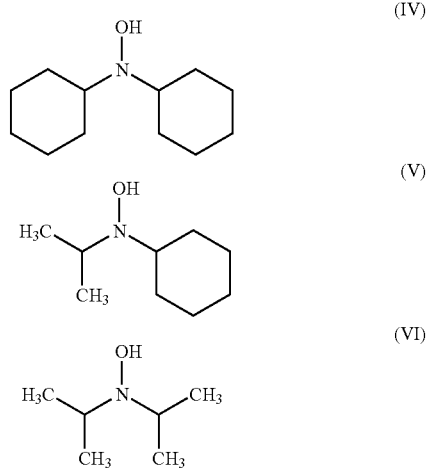

The starting materials for the process are readily obtainable ketones or, if appropriate, aldehydes and inexpensive, readily available hydroxylamine or a suitable salt of hydroxylamine. This allows great flexibility in the syntheses, since a wide range of ketones and aldehydes is available and it is not necessary to isolate any intermediates such as the oximes.

The process of the present invention prepares symmetrically or asymmetrically substituted N,N-dihydrocarbylhyrdoxylamines by reacting one or two ketones or one aldehyde and one ketone and hydroxylamine or a salt of hydroxylamine in the presence of hydrogen and a hydrogenation catalyst.

In a preferred embodiment of the process of the invention, a compound of the general formula (II) is used in step a) and a compound of the general formula (III) is used in step c). In a further preferred embodiment, the compounds of the general formulae (II) and (III) are ketones.

DETAILED DESCRIPTION OF THE INVENTION

The individual steps of the process are described below. In a preferred embodiment of the process of the invention, the steps a), b) and c) are carried out in a single reactor without isolation and/or purification of the intermediates.

Step a):

In step a) of the process of the invention, hydroxylamine H$_2$NOH or a salt of hydroxylamine is reacted with a compound of the general formula (II) or (III)

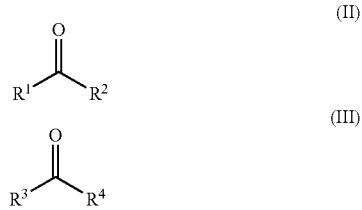

where $R^1$, $R^2$, $R^3$ and $R^4$ are as defined in formula (I).

In step a) of the process of the invention, it is usual to react a compound of the general formula (II) or (III) with hydroxylamine or a salt of hydroxylamine, with a compound of the general formula (II) and hydroxylamine being shown by way of example in the reaction scheme:

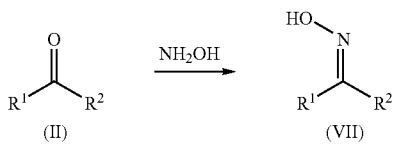

In step a), a ketone or aldehyde and hydroxylamine or a salt of hydroxylamine are converted into the corresponding oxime (VII) or the salt of the corresponding oxime.

The compounds of the general formulae (II) and (III) are ketones or aldehydes. Either a ketone, two different ketones or a ketone and an aldehyde are used in the process of the invention.

In a preferred embodiment of the process of the invention, a salt of hydroxylamine is used in step a). In a particularly preferred embodiment, hydroxylamine is used in the form of its hydrochloride or its hemisulfate in step a).

The ratio of hydroxylamine to the compound of the general formula (II) or (III) is dependent on whether symmetrical or unsymmetrical compounds of the general formula (I) are prepared in the process of the invention.

If unsymmetrical compounds of the general formula (I) are prepared, the molar ratio of hydroxylamine or a salt of hydroxylamine to the compound of the general formula (II) or (III) in step a) is generally 1.5:0.8, preferably 1.4:0.9, particularly preferably 1.3:1.0.

If symmetrical compounds of the general formula (I) are prepared, the molar ratio of hydroxylamine or a salt of hydroxylamine to the compound of the general formula (II) or (III) in step a) is generally 0.5:5, preferably 0.8:4, particularly preferably 1.0:2.0 to 3.0.

Step a) of the process of the invention can generally be carried out in all reactors known to those skilled in the art; examples which may be mentioned are: reactors made of glass and/or metal, preferably stainless steel, preferably having a volume of from 0.5 to 50 l. The reactors are equipped with suitable stirrers, for example disk stirrers with baffles. In step a), it is possible for a compound of the general formula (II) or (III) to be initially charged and hydroxylamine or a salt of hydroxylamine to be added. However, it is also possible for the reverse order to be employed, i.e. for hydroxylamine or a salt of hydroxylamine to be initially charged and a compound of the general formula (II) or (III) to be added. Furthermore, it is possible for the catalyst comprising a noble metal from step b) to be initially charged in step a), and hydroxylamine or salt of hydroxylamine and then ketone or ketones and, if appropriate, aldehyde to be added.

Step a) of the process of the invention is, in a preferred embodiment, carried out in an acidic solvent, particularly preferably in an acidic, aqueous solvent. Use of a salt of hydroxylamine results in the reaction solution being acidified by liberation of the corresponding acid. If no salt of hydroxylamine is added in step a), acid, for example hydrochloric acid or sulfuric acid, can be added in the process of the invention.

In a particularly preferred embodiment, step a) of the process of the invention is carried out in an acidic, aqueous solvent.

The solvent used according to the invention can also comprise alcohols. Suitable alcohols or mixtures comprising alcohol are: lower alcohols such as $C_1$-$C_3$-alcohols, e.g. methanol, ethanol, isopropanol, propanol, methanol/ethyl acetate mixtures, methanol/methylene chloride mixtures, ethanol/ethyl acetate mixtures, alcohol/tetrahydrofuran mixtures and higher alcohols, such as $C_4$-$C_{10}$-alcohols, e.g. n-octanol, isobutanol, if appropriate in admixture with water. If alcohol is comprised in the solvent in step a) of the process of the invention, it is present in an amount of from 50 to 80% by weight.

Step a) is preferably carried out at a temperature of from 0 to 70° C., particularly preferably from 25 to 70° C., very particularly preferably from 40 to 65° C.

Step b):

In step b), the oxime formed in step a) is hydrogenated in the presence of a catalyst comprising a noble metal to a hydrogen consumption of from 60 to 130 mol % of theory, preferably from 90 to 120 mol %, particularly preferably from 105 to 110 mol %, giving the corresponding monohydrocarbylhydroxylamine or the salt of the corresponding monohydrocarbylhydroxylamine.

It has been found that carrying out the hydrogenation with monitoring of the hydrogen consumption enables the proportion of undesirable by-products to be reduced.

In step b), an oxime (VII) or a salt of the oxime and hydrogen are reacted in the presence of a catalyst to form the corresponding monohydrocarbylhydroxylamine (VIII) or a salt of the corresponding monohydrocarbylhydroxylamine, with a compound of the general formula (VII) being shown by way of example as substrate in the reaction scheme.

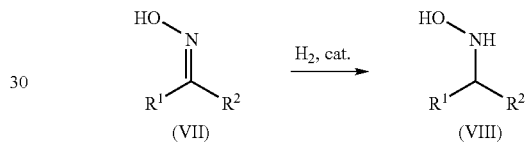

In a preferred embodiment, the reaction mixture from step a) is used without further work-up in step b). Step b) is particularly preferably carried out immediately subsequent to step a) in the same reactor. In a particularly preferred embodiment, the ketone is added to the mixture of hydroxylamine or a salt of hydroxylamine and the catalyst in step a) of the process of the invention and hydrogen is then introduced into the reactor in step b) of the process of the invention.

If unsymmetrical compounds of the general formula (I) are prepared in the process of the invention, the molar ratio of oxime of the general formula (VII) to the compound of the general formula (II) or (III) in step b) is generally 0.5:1.5, preferably 0.7:1.3, particularly preferably 1.0:1.0.

In a preferred embodiment, step b) of the process of the invention is carried out at a temperature of from 0 to 70° C., particularly preferably from 25 to 70° C., very particularly preferably from 40 to 65° C.

In a further preferred embodiment, the hydrogenation in step b) of the process of the invention is carried out at a pressure of from 1 to 100 bar, preferably from 1 to 10 bar, particularly preferably from 1 to 3 bar.

In a preferred embodiment, the noble metal is selected from the group of the platinum metals. The group of the platinum metals comprises platinum, palladium, rhodium, ruthenium, osmium and iridium. Particular preference is given to using platinum or palladium as catalytically active metal.

A catalyst in which the catalytically active metal has been applied to an appropriate support is preferably used in the process of the invention. The material of the support is preferably selected from the group consisting of silicon dioxide, aluminum oxide, titanium oxide, carbon, graphite and mixtures thereof, particularly preferably graphite.

The catalytically active metal can generally be applied to the support by all methods known to those skilled in the art, for example impregnation of the support with a solution, for example an aqueous solution, of a compound comprising the active metal with subsequent drying and reduction, vapor deposition of the catalytically active metal onto the support or precipitation. The elemental metal or a compound of the metal, preferably an oxide, can be used as catalytically active component.

In a preferred embodiment, the proportion of noble metal on the support is from 0.3 to 15.0% by weight, preferably from 0.3 to 3.0% by weight, particularly preferably from 0.3 to 1% by weight.

Typical noble metal hydrogenation catalysts which are used in the present process include 5% of platinum on carbon, 10% of platinum on carbon, platinum oxide, a combination of 5% of platinum on carbon with platinum oxide and 5% of palladium on carbon.

The catalytically effective amount of the catalyst is from 0.001 to 1 mol %, preferably from 0.01 to 0.5 mol %, particularly preferably from 0.02 to 0.1 mol %, based on the ketone or the aldehyde. A catalyst comprising platinum is preferred.

It is possible for step a) and step b) to be carried out in succession in the process of the invention, i.e. ketone or aldehyde and hydroxylamine or a salt of hydroxylamine are combined and reacted, after which the catalyst is added and the mixture is hydrogenated in a hydrogen atmosphere. However, it is also possible for hydroxylamine or a salt of hydroxylamine, ketone or aldehyde and hydrogenation catalyst to be reacted simultaneously in a hydrogen atmosphere.

The product obtained in step b) can generally be isolated and/or purified by all methods known to those skilled in the art. Step c) preferably follows without prior isolation and/or purification of the product from step b).

Step b) of the process of the invention is complete when the appropriate amount of hydrogen has been consumed. This is generally the case after from about 30 minutes to 12 hours.

Step c):

In step c) the monohydrocarbylhydroxylamine derivative formed in step b) is reacted with at least one equivalent, preferably one equivalent, of the compound of the general formula (II) or (III) and the reaction mixture is hydrogenated in the presence of a catalyst comprising a noble metal to a hydrogen consumption of from 60 to 130 mol % of theory, preferably from 90 to 120 mol %, particularly preferably from 100 to 110 mol %, forming the corresponding dihydrocarbylhydroxylamine or the salt of the corresponding dihydrocarbylhydroxylamine.

In step c) of the process of the invention, too, carrying out the hydrogenation with monitoring of the hydrogen consumption makes it possible to reduce the proportion of undesirable by-products.

In step c) of the process of the invention, a monohydrocarbylhydroxylamine derivative is reacted with a compound of the general formula (II) or (III) and the reaction mixture is hydrogenated in the presence of a catalyst comprising a noble metal so as to form the corresponding dihydrocarbylhydroxylamine or the salt of the corresponding dihydrocarbylhydroxylamine, with a compound of the general formula (VIII) and a compound of the general formula (III) being shown by way of example as substrates in the reaction scheme.

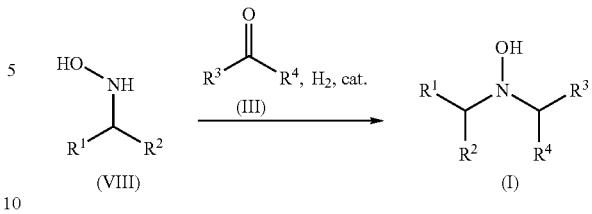

In step c), a monohydrocarbylhydroxylamine (VIII) or a salt of the monohydrocarbylhydroxylamine and a further ketone or aldehyde (III) are reacted in the presence of hydrogen and a catalyst to form the corresponding dihydrocarbylhydroxylamine (I) or a salt of the corresponding dihydrocarbylhydroxylamine by reductive coupling.

If an aldehyde is introduced in step a), a ketone is introduced in step c).

Step c) is preferably carried out in the same reactor as the steps a) and b), so that ketone or if appropriate aldehyde is added to the reaction mixture from step b) without the reaction mixture being isolated and/or purified.

The reaction of the monohydrocarbylhydroxylamine or the salt of the monohydrocarbylhydroxylamine with a ketone or if appropriate an aldehyde is hydrogenated in step c) in the presence of a catalyst comprising a noble metal to a hydrogen consumption of from 60 to 130 mol %, preferably from 90 to 120 mol %, particularly preferably from 100 to 110 mol %, of theory.

The hydrogenation is carried out in a manner analogous to the hydrogenation in step b). Step c) is preferably carried out using the same catalyst as in step b), i.e. the hydrogenation catalyst still present from step b) is also used again in this step, and hydrogenation is carried out by introduction of hydrogen.

As regards the solvent, the temperatures prevailing in the process and the pressure, what has been said above for steps a) and b) applies. Since steps a), b) and c) are preferably carried out in succession in the same reactor, preference is also given to using the same solvent in steps a), b) and c).

In a very particularly preferred embodiment, steps a) to c) are carried out in the same reactor without isolation and/or purification of the intermediates in a constant hydrogen atmosphere (one-pot process).

When hydrogen uptake ceases, in general after from about 30 minutes to 12 hours, the catalyst is generally removed by filtration. The filtrate is usually evaporated to remove the solvent present.

In a preferred embodiment of the process of the invention, the temperature in steps a), b) and c) is from 0 to 100° C., preferably from 25 to 70° C., particularly preferably from 40 to 65° C.

In a preferred embodiment of the process of the invention, steps a), b) and c) are carried out in the solvent which is used in step a). Thus, steps a), b) and c) of the process of the invention are carried out in an acidic, aqueous solvent in a preferred embodiment. In a further preferred embodiment, the acidic, aqueous solvent comprises one or more alcohols.

Step d):

If a salt of hydroxylamine was used in step a), the salt of the dihydrocarbylhydroxylamine formed is reacted with a base, preferably sodium hydroxide and/or potassium hydroxide, in the optional step d).

Step d) is carried out only when a salt of hydroxylamine is used in step a) of the process of the invention.

If the product is a liquid, it can, if appropriate, be purified by generally known methods such as distillation, chromatography, washing and/or extraction.

If the product of the process of the invention is a solid, it is generally isolated by filtration and purified by recrystallization. As an alternative, the product can be isolated by extraction of the alkali solution with an organic solvent such as ethyl acetate or methylene chloride and it can then be purified if necessary.

Examination of the crude product of the present process by means of 1H-NMR shows that the products generally have a purity of greater than 90%. Further purification by recrystallization, etc., is thus generally not necessary.

The ketones, aldehydes and hydroxylamine or salts of hydroxylamine used in the process of the invention are commercially available or can easily be prepared by methods known to those skilled in the art.

The invention will now be described in further detail with reference to the following non-limiting examples.

EXAMPLES

The experiments are carried out in standard miniplant reactors having a size of 0.75 and 2.5 liters. The reactors have a disk stirrer having six blades and a gas inlet tube which introduces the gas below the stirrer. The energy input due to the stirrer is about 4 W/l. The catalyst used comprises platinum as catalytically active metal. Hydrogenation is carried out at atmospheric pressure. $^1$H-NMR and titration are used as analytical methods.

Example 1

Preparation of dicyclohexylhydroxylamine hemisulfate (DCHAS)

An aqueous solution of 1346 g of hydroxylammonium sulfate solution (24.4% strength) is made up (=4.00 mol of hydroxylamine). 79.0 g of moist hydrogenation catalyst are added thereto. While stirring, 477.9 g (4.87 mol) of cyclohexanone are introduced at room temperature over a period of 30 minutes by means of a Desaga pump. This results in the internal temperature rising to 38.2° C. The reactor is flushed with H2 and the hydrogenation is subsequently commenced at 60° C. The hydrogen is introduced via the sparging tube during the entire time. After about 3 hours, 103% of the theoretical amount of $H_2$ have been taken up and, in accordance with the CHAS content determined (by $^1$H-NMR), another 255.2 g (2.6 mol) of cyclohexanone are introduced by means of the Desaga pump. Hydrogenation is subsequently continued at 60° C. (with H2 flushing) until the theoretical amount of hydrogen (2.6 mol of the anion added) is reached.

It can be seen from the NMR spectrum which is then measured that DCHAS has been formed. Traces of oxime, ammonium sulfate, CHAS, cyclohexylamine hemisulfate and dicyclohexylamine hemisulfate can be discerned as impurities in the NMR spectrum.

The catalyst is filtered off and the filtrate is freed of residual oxime by washing with toluene. After evaporation, the DCHAS can finally be obtained as a colorless solid by crystallization at low temperature. The purity is about 90-95%.

Example 2

Preparation of cyclohexylisopropylhydroxylamine hemisulfate (CIPHAS)

An aqueous solution of 1800 g of hydroxylammonium sulfate solution (25% strength) is made up (=5.39 mol of hydroxylamine). 79.0 g of moist hydrogenation catalyst are added thereto. The free sulfuric acid in the solution is partly neutralized by means of 36.7 g of 50% strength sodium hydroxide solution (=0.458 mol) over a period of 2 minutes. While stirring, the mixture is thermostated to 50° C. and 477.9 g (4.87 mol) of cyclohexanone are introduced over a period of 30 minutes by means of a Desaga pump. The reactor is flushed and the hydrogenation is commenced with vigorous stirring. The hydrogen is introduced via the sparging tube during the entire time. After 100% of theory of $H_2$ have been reached, 167 g (2.88 mol) of acetone are fed in at 50° C. Hydrogenation is subsequently continued. Finally, CIPHAS is confirmed as main product. The free hydroxylamine derivative can be obtained by reaction with sodium hydroxide. A work-up is not carried out.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims

What is claimed is:

1. A process for preparing an N,N-dihydrocarbylhydroxylamine of the general formula (I):

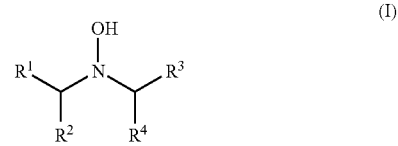

wherein $R^1$, $R^2$, $R^3$ and $R^4$ each independently represent a moiety selected from the group consisting of branched or unbranched aliphatic, cycloaliphatic, heteroaromatic and aromatic radicals having from 1 to 32 carbon atoms, or $R^1$ and $R^2$ and/or $R^3$ and $R^4$ are joined to form a ring having a total of from 3 to 12 carbon atoms, the process comprising:

a) reacting hydroxylamine $H_2NOH$ or a salt of hydroxylamine with a compound of the general formula (II) or (III)

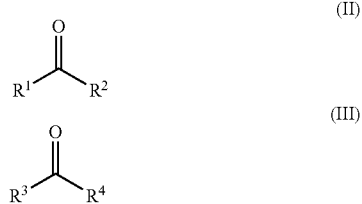

where $R^1$, $R^2$, $R^3$ and $R^4$ are as defined in formula (I) to form an oxime intermediate, b) hydrogenating the oxime intermediate in the presence of a catalyst comprising a noble metal to a hydrogen consumption of from 60 to 130 mol % of theory, to form a corresponding monohydrocarbylhydroxylamine or a salt of the corresponding monohydrocarbylhydroxylamine, and c) reacting the monohydrocarbylhydroxylamine or salt thereof with a compound of the general formula (II) or (III) with hydrogenation of the reaction mixture in the presence of a catalyst comprising a noble metal to a hydrogen consumption of from 60 to 130 mol % of theory, forming a corresponding dihydrocarbylhydroxylamine or a salt of the corresponding dihydrocarbylhydroxylamine, with the proviso that where a salt of hydroxylamine is reacted with a compound of the general formula (II) or (III), the process further comprises reacting of the salt of dihydrocarbylhydroxylamine with a base.

2. The process according to claim 1, wherein the radicals $R^1$, $R^2$, $R^3$ and $R^4$ are identical.

3. The process according to claim 1, wherein the radicals $R^1$ and $R^2$ and to radicals $R^3$ and $R^4$ are in each case identical and the radicals $R^1$ and $R^3$ and the radicals $R^2$ and $R^4$ are different from one another.

4. The process according to claim 1, wherein $R^1$ and $R^2$ and/or $R^3$ and $R^4$ form a ring which in each case has a total of from 3 to 12 carbon atoms.

5. The process according to claim 1, wherein a compound of the general formula (II) is used in step a) and a compound of the general formula (III) is used in step c).

6. The process according to claim 1, wherein $R^1/R^2$ and $R^3/R^4$ in the compounds of the general formulae (I), (II) and (III) in each case form a saturated ring having 6 carbon atoms.

7. The process according to claim 1, wherein $R^1$, $R^2$, $R^3$ and $R^4$ in the compounds of the general formulae (I) (II) and (III) are selected from the group consisting of methyl, ethyl, n-propyl, isopropyl, n-butyl, isobutyl and pentyl.

8. The process according to claim 1, wherein $R^1$ and $R^2$ are each methyl and $R^3$ and $R^4$ form a saturated ring having 6 carbon atoms.

9. The process according to claim 1, wherein the noble metal in step b) and c) has been applied to a support comprising a material selected from the group consisting of silicon dioxide, aluminum oxide, titanium oxide, carbon, graphite and mixtures thereof.

10. The process according to claim 9, wherein the proportion of noble metal on the support is from 0.3 to 15.0% by weight.

11. The process according to claim 1, wherein the noble metal is selected from the group of the platinum metals.

12. The process according to claim 1, wherein the temperature in steps a), b) and c) is from 0 to 100° C.

13. The process according to claim 1, wherein hydroxylamine is used in the form of its hydrochloride or its hemisulfate.

14. The process according to claim 1, wherein steps a), b) and c) are carried out in an acidic, aqueous solvent.

15. The process according to claim 14, wherein the acidic, aqueous solvent comprises one or more alcohols.

16. The process according to claim 1, wherein the hydrogenation is carried out at a pressure of from 1 to 100 bar.

* * * * *